United States Patent
Weser et al.

(10) Patent No.: US 9,132,072 B2
(45) Date of Patent: *Sep. 15, 2015

(54) COLORING AGENT HAVING DIRECT DYES AND NON-IONIC SURFACTANTS

(71) Applicant: Henkel AG & Co. KGaA, Düsseldorf (DE)

(72) Inventors: Gabriele Weser, Neuss (DE); Claudia Kolonko, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/310,903

(22) Filed: Jun. 20, 2014

(65) Prior Publication Data

US 2014/0298598 A1    Oct. 9, 2014

Related U.S. Application Data

(63) Continuation of application No. PCT/EP0212/074487, filed on Dec. 5, 2012.

(30) Foreign Application Priority Data

Dec. 20, 2011   (DE) ............ 10 2011 089 219

(51) Int. Cl.

| | | |
|---|---|---|
| *A61Q 5/10* | (2006.01) | |
| *A61K 8/41* | (2006.01) | |
| *A61K 8/35* | (2006.01) | |
| *A61K 8/39* | (2006.01) | |
| *A61K 8/60* | (2006.01) | |
| *A61Q 5/06* | (2006.01) | |
| *A61K 8/86* | (2006.01) | |

(52) U.S. Cl.
CPC .................. *A61K 8/416* (2013.01); *A61K 8/355* (2013.01); *A61K 8/39* (2013.01); *A61K 8/604* (2013.01); *A61K 8/86* (2013.01); *A61Q 5/065* (2013.01); *A61Q 5/10* (2013.01); *A61K 2800/4324* (2013.01)

(58) Field of Classification Search
CPC ............ A61Q 5/10; A61K 8/37; A61K 8/41; A61K 8/86; A61K 8/602; A61K 8/604; C09B 1/207
USPC ............................... 8/405, 552, 580, 582, 643
See application file for complete search history.

(56) References Cited

U.S. PATENT DOCUMENTS

| | | | | |
|---|---|---|---|---|
| 8,298,296 | B2* | 10/2012 | Wood et al. | 8/405 |
| 8,506,650 | B2* | 8/2013 | Hashimoto et al. | 8/405 |
| 2001/0002254 | A1* | 5/2001 | Duffer et al. | 424/70.1 |
| 2004/0034945 | A1 | 2/2004 | Javet et al. | |
| 2013/0156716 | A1* | 6/2013 | Yontz | 424/70.6 |

FOREIGN PATENT DOCUMENTS

| | | | | |
|---|---|---|---|---|
| CA | 2613049 | * | 11/2007 | ............ A61Q 5/10 |
| CA | 2613049 | A1 | 4/2008 | |
| CA | 2646866 | A1 | 3/2009 | |
| DE | 2026096 | A1 | 12/1970 | |
| DE | 2117251 | A1 | 10/1971 | |
| DE | 3511209 | A1 | 10/1986 | |
| EP | 0852136 | A1 | 7/1998 | |
| EP | 1006154 | B1 | 6/2000 | |
| EP | 1820826 | | 8/2007 | |
| EP | 2329809 | A1 | 6/2011 | |
| EP | 2468245 | A1 | 6/2012 | |
| GB | 1123095 | A | 8/1968 | |

OTHER PUBLICATIONS

STIC Search Report dated Sep. 2, 2014.*
A. H. Saiyad et al: "Physicochemical properties of mixed surfacant systems: sodium dodecyl benzene sulfonate with triton X 100", Colloid and Polymer Science, (Oct. 19, 1998), pp. 913-919.

* cited by examiner

*Primary Examiner* — Eisa Elhilo
(74) *Attorney, Agent, or Firm* — Steven L. Nichols; Van Cott, Bagley, Cornwall & McCarthy P.C.

(57) ABSTRACT

The present specification provides an agent for coloring keratinic fibers, wherein it contains (a) at least one compound of formula (I) and (b) at least one non-ionic surfactant. The present disclosure also provides a method of using such an agent as a coloring composition for human hair, wherein the method comprises application of the agent to the hair, an application time of from 5 to 45 minutes, and rinsing the agent from the hair.

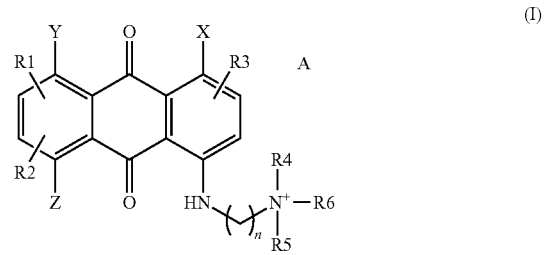

(I)

18 Claims, No Drawings

COLORING AGENT HAVING DIRECT DYES AND NON-IONIC SURFACTANTS

RELATED DOCUMENTS

The present application claims the benefit and is a U.S. continuation patent application under 35 U.S.C. 111(a) and claims the right of priority under 35 U.S.C. 365 to international patent Application No. PCT/EP2012/074487, filed Dec. 5, 2012, entitled "Coloring Agent having Direct Dyes and Non-Ionic Surfactants" which claims benefit of German application No.: 102011089219.2, filed Dec. 20, 2011, these applications are herein incorporated by reference in their entirety.

FIELD OF THE INVENTION

The present specification relates generally to agents for coloring and optionally lightening keratinic fibers. More specifically, the present application relates to cosmetic agents including specific cationic anthraquinone dyes and special non-ionic surfactants. The present specification also relates to the use of these agents to produce hair colors having increased shine, an intense color result, improved fastness properties and reduced selectivity.

As a general rule, either substantive dyes or oxidation dyes are used for coloring keratinic fibers. Although intense colors with good fastness properties may be obtained with oxidation dyes, the development of the color generally takes place under the influence of oxidizing agents such as $H_2O_2$ for example, which in some cases may result in damage to the fiber. Furthermore, some oxidation dye precursors or certain mixtures of oxidation dye precursors may have a sensitizing effect on people with sensitive skin. Substantive dyes are applied under gentler conditions. The disadvantage of these dyes, however, lies in the fact that the colors often have inadequate fastness properties, in particular with regard to hair washing, but also with respect to external influences, such as sunlight, or reactive environmental chemicals, such as swimming pool water, for example. Such colors are also generally significantly more sensitive to shampooing than oxidative colors, such that an often undesired shift in shade or even a visible "decolorization" occurs much more quickly.

Achieving a uniform coloring of hair that has been frequently treated, such as for example bleached or permanently waved hair, where the fibers present differing degrees of pre-existing damage in the various lengths or variously treated areas, represents a particular challenge in terms of coloring hair with substantive dyes. During the coloring process itself, the coloring agent may exhibit an uneven coloring behavior on hair with differing degrees of pre-existing damage, while repeated hair washing may also cause the dyes to be washed out of the different areas of the hair to varying degrees, resulting in an inconsistent, and hence undesirable color result.

In the development of coloring products based on substantive dyes there is still a particular focus on producing dye formulations having reduced selectivity, meaning that a uniform color result may be achieved on sections of the hair having varying degrees of pre-existing damage. In particular, this reduced selectivity should still be present not only immediately after the coloring process, but also after repeated hair washes.

An object of the present specification is therefore to provide a coloring agent for keratinic fibers, in particular human hair, which, in addition to other positive fastness properties, has in particular a low selectivity (or a good equalizing capacity) and good wash fastness.

The colors achieved with the agents according to the present specification should deliver a brilliant and intense color result, both immediately after the coloring process and after repeated hair washes. Following application of the coloring agent the hair should be uniformly colored, even in cases where the hair exhibits varying degrees of pre-existing damage, and this uniformity in the color result should still be present even after repeated hair washes. In particular, brilliant and neutral blue shades or shades in the blue region with the advantageous fastness properties described above should be achieved, said shades also being outstandingly suitable for matting. The agents should additionally have an optimized viscosity in terms of both the application process and the coloring capacity.

The use of cationic anthraquinone dyes in products for coloring keratinic fibers is already known in principle from the prior art, for example from EP 1 006 154 B1 or EP 1 820 826 A1. Furthermore, combinations of cationic anthraquinone dyes with oxidation dye precursors of the developer type are claimed in EP 2 329 809 for the oxidative coloring of hair.

Surprisingly, it has been found that combinations of specific cationic anthraquinones as substantive dyes with special non-ionic surfactants lead to colors which achieve the object of the present specification to an outstanding degree.

Combinations of the specific cationic anthraquinones according to the first subject matter of the present specification with special non-ionic surfactants have not yet been described.

Furthermore, other desirable features and characteristics of the present invention will become apparent from the subsequent detailed description of the invention and the appended claims, taken in conjunction with this background of the invention.

BRIEF SUMMARY OF THE INVENTION

The present specification firstly provides an agent for coloring keratinic fibers comprising, in a cosmetic carrier,
(a) at least one compound of formula (I):

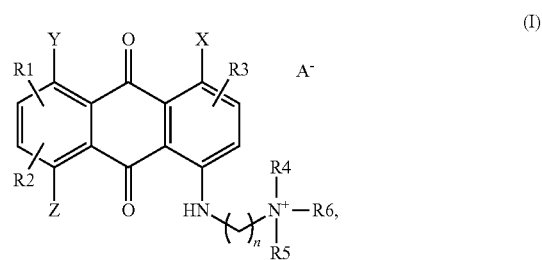

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

wherein at least one of the residues X, Y and Z denotes an N(R7)(R8) group;

n denotes an integer between 2 and 6 inclusive; and

A⁻ denotes a physiologically acceptable anion;

and (b) at least one non-ionic surfactant.

The present specification secondly provides a method of using a cosmetic agent for coloring keratinic fibers. The method comprises:

(A) applying an agent for coloring, and optionally simultaneously lightening, keratinic fibers comprising, in a cosmetic carrier, a. at least one compound of formula (I):

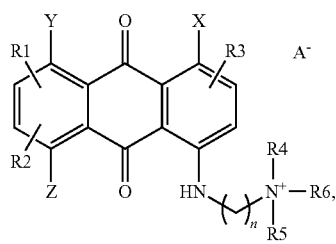

in which:

R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;

R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

or R4 and R5, together with the quaternary nitrogen atom to which they are bound, form a 5-, 6- or 7-membered ring, which optionally includes further heteroatoms and optionally also bears further substituents;

X, Y, Z each independently of one another, denote hydrogen, a hydroxyl group or an N(R7)(R8) group, in which:

R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

wherein at least one of the residues X, Y and Z denotes an N(R7)(R8) group;

n denotes an integer between 2 and 6 inclusive; and

A⁻ denotes a physiologically acceptable anion; and b. at least one non-ionic surfactant; and (B) allowing the agent to act on the hair for a period from 5 to 45 minutes; and (C) rinsing the hair.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In the context of the present specification, "keratinic fibers," "keratin fibers," or similar terminology is understood to mean all animal hair, for example fur, wool, feathers, and in particular, human hair. Although the agents according to the present specification are primarily suitable for dyeing keratin fibers, there is nothing in principle to preclude their use in other fields.

The term "coloring of keratin fibers" in the context of the present specification includes any form of color changing of fibers. It includes in particular the color changes covered by the terms tinting, lightening, bleaching, peroxiding, oxidative coloring, semipermanent coloring, permanent coloring and temporary coloring. It also includes color changes according to the present specification presenting a lighter color result in comparison to the original color, such as, for example, combined coloring and bleaching processes.

The agents according to the present specification include the active agents in a cosmetic carrier, preferably in a suitable aqueous, alcoholic or aqueous-alcoholic carrier. For the purposes of hair coloring, such carriers are for example creams, emulsions, gels or surfactant-containing foaming solutions, such as for example shampoos, foam aerosols, foam formulations or other preparations which are suitable for use on the hair. It is also possible, however, for the agents according to the present specification to be integrated into a formulation in powder or tablet form.

In the context of the present specification, aqueous-alcoholic solutions are understood to be aqueous solutions including 3 to 70 weight percent (wt. %) of a $C_1$ to $C_4$ alcohol, in particular ethanol or isopropanol. The agents according to the present specification may additionally include further organic solvents, such as for example methoxybutanol, benzyl alcohol, ethyl diglycol or 1,2-propylene glycol. All water-soluble organic solvents are preferred here. In the context of the present specification, an aqueous carrier includes at least 30 wt. %, in particular at least 50 wt. % of water, relative to the total weight of the agent. Aqueous carriers are preferred according to the present specification, such that the agent has at least 80 wt. % water, preferably at least 85 wt. % water, relative to the total weight of the agent.

The first essential ingredient (a) of the agents according to the present specification is at least one substantive cationic anthraquinone dye of general formula (I).

The substituents R1 to R8 of the compound of formula (I) are described below by way non-limiting examples: Examples of a $C_1$-$C_6$ alkyl group are the methyl, ethyl, propyl, isopropyl, n-butyl, s-butyl and t-butyl, n-pentyl and n-hexyl groups. Propyl, ethyl and methyl are preferred alkyl residues. Examples of a $C_2$-$C_6$ alkenyl group are vinyl, allyl, but-2-enyl, but-3-enyl and isobutenyl, preferred $C_2$-$C_6$ alkenyl residues being vinyl and allyl. Preferred examples of a $C_1$-$C_6$ hydroxyalkyl group are a hydroxymethyl, 2-hydroxyethyl, 2-hydroxypropyl, 3-hydroxypropyl, 4-hydroxybutyl, 5-hydroxypentyl and 6-hydroxyhexyl group; a 2-hydroxyethyl group is particularly preferred. $C_1$-$C_6$ alkoxy groups that are preferred according to the present specification are the methoxy or ethoxy group. Examples of halogen atoms are F, Cl, Br or I atoms, with Br or Cl atoms being most particularly preferred. Preferred examples of $C_1$-$C_6$ alkoxy $C_2$-$C_6$ alkyl groups according to the present specification are the methoxyethyl, ethoxyethyl, methoxypropyl, methoxybutyl, ethoxypropyl, ethoxybutyl and methoxyhexyl group. Examples of a $C_1$-$C_6$ acyl amino group are the acetamide group, the propanamide group and the butanamide group, the acetamide group being preferred. The pyrrolidinium ring, the piperidinium ring, the morpholinium ring and the 1-azepanium ring may be mentioned as preferred examples of a 5-, 6- or 7-membered ring formed from R4, R5 and the quaternary nitrogen atom.

Dyes of formula (I) in which R1, R2 and R3, independently of one another, denote hydrogen, halogen, a carboxyl group, a sulfonic acid group, a $C_1$-$C_6$ alkyl group or a $C_1$-$C_6$ alkoxy group deliver particularly intense color results and are therefore preferred.

It is furthermore preferable for one of the residues selected from R1, R2 and R3 to denote halogen, a carboxyl group, a sulfonic acid group, a $C_1$-$C_6$ alkyl group or a $C_1$-$C_6$ alkoxy group and for the other two residues selected from R1, R2 and R3 both to denote hydrogen.

A preferred example of the first subject matter of the present specification is an agent for coloring, and optionally lightening, keratinic fibers, which is characterized in that it includes a compound of formula (I) in which at least one of the residues R1, R2 and/or R3 denotes a $C_1$-$C_6$ alkyl group.

In the case of particularly suitable compounds of formula (I), one of the residues selected from R1, R2 and R3 denotes a $C_1$-$C_6$ alkyl group and the other two residues selected from R1, R2 and R3 denote hydrogen.

In an most particularly preferred example, R1 and R2 both denote a hydrogen atom and R3 denotes a methyl group.

Furthermore, particularly good coloring results are obtained with agents including at least one compound of formula (I) in which the residues R4, R5 and R6, independently of one another, denote a $C_1$-$C_6$ alkyl group or an alkenyl group. In particular, each of the residues R4, R5 and R6 preferably denotes a $C_1$-$C_6$ alkyl group.

It is most particularly preferable for R4 and R5 both to denote a methyl group and for R6 to denote a methyl group, an ethyl group or an n-propyl group.

It is also most particularly preferable for R4 and R5 both to denote a methyl group and for R6 to denote an n-propyl group.

In a likewise particularly preferred example the residues R4, R5 and R6 each denote a methyl group.

For compounds of formula (I), there is the proviso that at least one of the residues X, Y and Z denotes an N(R7)(R8) group. Colors having good application properties were obtained in particular when compounds of formula (I) were used in which X denotes an N(R7)(R8) group and Y and Z each denote hydrogen. R7 and R8, preferably (and independently of one another) denote hydrogen or a $C_1$-$C_6$ alkyl group. R7 and R8, particularly preferably (also independently of one another) denote hydrogen or a methyl group. Compounds of formula (I) in which both R7 and R8 denote hydrogen have proved to be particularly suitable and are therefore particularly preferred.

In the context of the work leading to the agents of this disclosure it has proved most particularly advantageous for X to denote an $NH_2$ group.

A further preferred example is therefore an agent for coloring, and optionally lightening, keratinic fibers, which is characterized in that it includes a compound of formula (I) in which at least X denotes an $NH_2$ group.

n preferably denotes the numbers 2 or 3 and most particularly preferably the number 3.

$A^-$ denotes a physiologically acceptable anion. Suitable physiologically acceptable anions are halide, hydrogen sulfate, sulfate, benzenesulfonate, p-toluenesulfonate, acetate, citrate, lactate, tartrate, methosulfate ($H_3COSO_3^-$), methyl sulfonate or trifluoromethane sulfonate. $A^-$ particularly preferably denotes bromide or methosulfate ($H_3COSO_3^-$), with $A^-$ most particularly preferably denoting methosulfate ($H_3COSO_3^-$).

Agents for coloring, and optionally simultaneously lightening, keratinic fibers that are preferred according to the present specification are characterized in that they include at least one compound of general formula (I) selected from 3-[(4-amino-9,10-dihydro-3-methyl-9,10-dioxo-1-anthracenyl)amino]-N,N,N-trimethyl-1-propanaminium methosulfate, 3-[(4-amino-9,10-dihydro-3-methyl-9,10-dioxo-1-anthracenyl)amino]-N,N,N-trimethyl-1-propanaminium bromide, 3-[(4-amino-9,10-dihydro-3-methyl-9,10-dioxo-1-anthracenyl)amino]-N,N,N-trimethyl-1-propanaminium chloride, 3-[(4-amino-9,10-dihydro-3-methyl-9,10-dioxo-1-anthracenyl)amino]-N,N,N-trimethyl-1-propanaminium-p-toluenesulfonate, 3-[(4-amino-9,10-dihydro-3-methyl-9,10-dioxo-1-anthracenyl)amino]-N,N,N-trimethyl-1-propanaminium acetate, 3-{([9,10-dihydro-4-(methylamino)-9,10-dioxo-1-anthracenyl]amino}-N,N-dimethyl-N-propyl-1-propanaminium methosulfate, 3-{([9,10-dihydro-4-(methylamino)-9,10-dioxo-1-anthracenyl]amino}-N,N-dimethyl-N-propyl-1-propanaminium bromide, 3-{([9,10-dihydro-4-(methylamino)-9,10-dioxo-1-anthracenyl]amino}-N,N-dimethyl-N-propyl-1-propanaminium chloride, 3-{([9,10-dihydro-4-(methylamino)-9,10-dioxo-1-anthracenyl]amino}-N,N-dimethyl-N-propyl-1-propanaminium-p-toluenesulfonate and 3-{([9,10-dihydro-4-(methylamino)-9,10-dioxo-1-anthracenyl]amino}-N,N-dimethyl-N-propyl-1-propanaminium acetate.

The compound of formula (Ia) is ideally suitable for achieving the object according to the present specification,

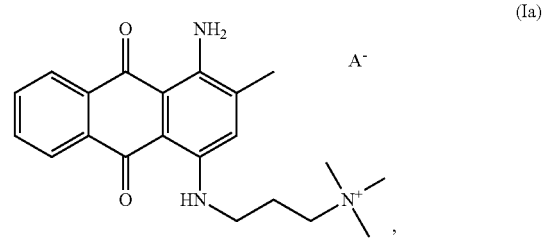

(Ia)

in which $A^-$ denotes a physiologically acceptable anion, preferably methosulfate ($H_3COSO_3^-$). The compound (Ia) in which $A^-$ denotes methosulfate is also known under the name Cationic Blue 347.

A further particularly preferred example is therefore an agent for coloring and optionally lightening keratinic fibers, which is characterized in that it includes as the compound of formula (I) a compound according to formula (Ia),

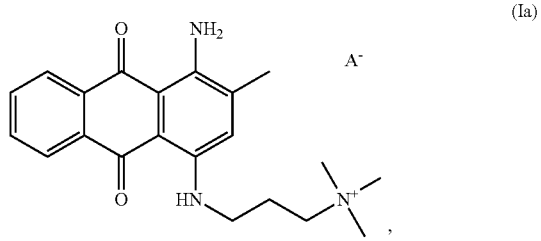

in which $A^-$ denotes a physiologically acceptable anion, preferably methosulfate ($H_3COSO_3^-$).

The agents according to the present specification for coloring, and optionally simultaneously lightening, keratin fibers include the compound(s) of formula (I) preferably in amounts above 0.0001 wt. % and below 5 wt. %, relative in each case to the total agent.

A further preferred example is an agent which includes the compound(s) of formula (I) in an amount of from 0.0001 to 5 wt. %, preferably from 0.005 to 3.5 wt. %, particularly preferably from 0.01 to 2.5 wt. %, in particular from 0.05 to 1.5 wt. %, and in particular preferably from 0.01 to 1.0 wt. %, relative in each case to the total weight of the agent.

As the second essential constituent of the formulation (b), the agents according to the present specification include at least one non-ionic surfactant, which may be selected from
(i) a polyethoxylated fatty alcohol having a degree of ethoxylation from 2 to 29;
(ii) an addition product of ethylene oxide and propylene oxide with one or more fatty alcohol;
(iii) a fatty acid glycol monoester, a fatty acid glyceryl monoester, or a sorbitan fatty acid ester, each of which may be optionally polyethoxylated;
(iv) alkyl polyglycosides; and
(v) combinations thereof.

In the context of the present specification, an ethoxylated fatty alcohol is understood to be an addition product of ethylene oxide with a fatty alcohol, wherein the degree of ethoxylation indicates the molar amount of ethylene oxide (EO) added on average per mol of fatty alcohol. Polyethoxylated fatty alcohols according to the present specification are preferably selected from polyethoxylated, linear or branched, saturated or unsaturated fatty alcohols, preferably having a chain length with 8 to 22 carbon atoms.

Preferred ethoxylated fatty alcohols are ethylene oxide addition products with decanol, lauryl alcohol, isotridecyl alcohol, myristyl alcohol, cetyl alcohol, palmoleyl alcohol, stearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof which form, for example, in the high-pressure hydrogenation of technical methyl esters based on fats and oils or aldehydes from the Roelen oxo synthesis, and as a monomer fraction in the dimerization of unsaturated fatty alcohols. Addition products with technical fatty alcohols or mixtures thereof having 12 to 18 carbon atoms, such as for example, coconut, palm, palm kernel or tallow fatty alcohol, in particular coconut and/or tallow fatty alcohol, are also preferred.

Depending on the production method, the ethoxylated fatty alcohols according to the present specification form as a mixture with a varying distribution of degree of ethoxylation. In the context of the present specification, these surfactants are therefore identified by the average degree of ethoxylation. This is conventionally indicated by a number after the fatty alcohol suffix "-eth" in the INCI name.

As well as ensuring an outstanding solubilizing power for the substantive dyes, polyethoxylated fatty alcohols having a degree of ethoxylation from 2 to 29 also serve to establish the optimum application viscosity.

To this end, the agents according to the present specification preferably include polyethoxylated fatty alcohols having a degree of ethoxylation from 2 to 29, preferably having a degree of ethoxylation from 2 to 25, more preferably from 3 to 20 and in particular from 5 to 12.

A further example of the first subject matter of the present specification is therefore an agent which is characterized in that it includes as the non-ionic surfactant at least one polyethoxylated fatty alcohol having a degree of ethoxylation from 2 to 25, preferably from 3 to 20 and in particular from 5 to 12.

Preferred ethoxylated fatty alcohols having an average degree of ethoxylation from 2 to 29 are for example Laureth-2, Oleth-2, Ceteareth-2, Laneth-2, Laureth-3, Oleth-3, Ceteareth-3, Laureth-4, Oleth-4, Ceteareth-4, Laneth-4, Laureth-5, Oleth-5, Ceteareth-5, Laneth-5, Deceth-7, Laureth-7, Oleth-7, Coceth-7, Ceteth-7, Ceteareth-7, C11-15 Pareth-7, Laureth-9, Oleth-9, Ceteareth-9, Laureth-10, Oleth-10, Beheneth-10, Ceteareth-10, Laureth-12, Ceteareth-12, Trideceth-12, Ceteth-15, Laneth-15, Ceteareth-15, Laneth-16, Ceteth-16, Oleth-16, Steareth-16, Oleth-20, Ceteth-20, Ceteareth-20, Laneth-20, Steareth-21, Ceteareth-23, Ceteareth-25, Ceteareth-27.

In addition to ethoxylated fatty alcohols, addition products of ethylene oxide and propylene oxide with fatty alcohols may also be used as suitable non-ionic surfactants according to the present specification. Suitable fatty alcohols have a chain length of at least 4 carbon atoms. The non-ionic surfactants which are addition products of ethylene oxide and propylene oxide with fatty alcohols preferably have a degree of ethoxylation from 2 to 75, preferably 5 to 50, more preferably 5 to 35, and a degree of propoxylation (mol of propylene oxide per mol of fatty alcohol; PPG) from 1 to 50, preferably 5 to 30. Preferred examples of such non-ionic surfactants are the compounds known under the INCI names PPG-5 Ceteth-20, PPG-6 Deceth-9, PPG-1 Trideceth-6, PPG-6 Deceth-4, PPG-1-Laureth-9; PPG-12-Laneth-50, PPG-5-Ceteth-20, PPG-12-Laneth-65, PPG-6 C12-18 PARETH-11, PPG-4 Laureth-2, PPG-4 Laureth-5, PPG-8 Deceth-6, PPG-6 $C_{12-18}$ Pareth-11, PPG-1-Laureth-9, PPG-5-Ceteth-20, PPG-5-Laureth-5, PPG-26-Buteth-26, PPG-20 Buteth-30, PPG-5 Buteth-7, PPG-12 Buteth-16, PPG-2 Buteth-3, PPG-3 Buteth-5, PPG-28 Buteth-35, PPG-33 Buteth-45, PPG-7 Buteth-10 and PPG-24-Buteth-27.

Further preferred non-ionic surfactants which may be used according to the present specification are optionally polyethoxylated fatty acid polyol esters of the fatty acid glycol monoester, fatty acid glyceryl monoester and/or sorbitan fatty acid ester types. Preferred examples of optionally polyethoxylated fatty acid glycol monoesters are PEG-100 stearate, PEG-90 stearate, PEG-50 stearate, PEG-30 stearate, PEG-10 stearate, PEG-7 stearate, PEG-100 oleate, PEG-90 oleate, PEG-50 stearate, PEG-30 oleate, PEG-10 oleate, PEG-7 oleate, PEG-100 cocoate, PEG-90 cocoate, PEG-50 cocoate, PEG-30 cocoate, PEG-10 cocoate, and PEG-7 cocoate.

Preferred examples of optionally polyethoxylated fatty acid glyceryl monoesters are glyceryl stearate, PEG-30 glyceryl stearate, PEG-20 glyceryl stearate, glyceryl oleate, glyceryl cocoate, glyceryl palmitate, PEG-18 glyceryl oleate, PEG-18 glyceryl cocoate, PEG-7 glyceryl cocoate, PEG-30 glyceryl cocoate, and PEG-80 glyceryl cocoate.

Preferred examples of optionally polyethoxylated sorbitan fatty acid esters are the examples known under the INCI names Polysorbate-20 (sorbitan monolaurate+20 EO), Polysorbate-60 (sorbitan monostearate+20 EO), Polysorbate-65 (sorbitan tristearate+20 EO), Polysorbate-80 (sorbitan monooleate+20 EO), Polysorbate-85 (sorbitan trioleate+20 EO).

According to a preferred example, the agent includes at least one alkyl polyglucoside as the non-ionic surfactant. Alkyl polyglucosides are known non-ionic surfactants according to formula (II)

$$R^1O\text{-}[G]_p \qquad (II)$$

in which $R^1$ denotes an alkyl or alkenyl residue having 4 to 22 carbon atoms, G denotes a sugar residue having 5 or 6 carbon atoms and p denotes numbers from 1 to 10.

The alkyl polyglucosides may be derived from aldoses or ketoses having 5 or 6 carbon atoms, preferably from glucose. The index value p in the general formula (II) indicates the degree of polymerization (DP), i.e. the distribution of mono- and polyglucosides, and denotes a number between 1 and 10. Each individual molecule must always have an integer value of p; preferably, p may assume the values p=1 to 6 here. The value p for a particular alkyl polyglucoside is a calculated quantity determined by analysis, which is usually a fraction (as it describes the ensemble, rather than an individual molecule). Alkyl polyglucosides having an average degree of oligomerization p of 1.1 to 3.0 are preferably used. From an application perspective, alkyl polyglucosides having a degree of polymerization below 1.7, and in particular between 1.2 and 1.4, are preferred.

The alkyl or alkenyl residue $R^1$ may be derived from primary alcohols having from 4 to 11 carbon atoms, preferably from 8 to 10 carbon atoms. Typical examples are butanol, hexanol, octanol, decanol and undecanol as well as the technical mixtures thereof, such as are obtained for example in the hydrogenation of technical fatty acid methyl esters or during the hydrogenation of aldehydes from the Roelen oxo synthesis. Preference is given to alkyl polyglucosides with a chain length of $C_8$-$C_{10}$ (DP=1 to 3) which occur as the first flush in the separation by distillation of technical $C_8$-$C_{18}$ coconut fatty alcohol and which may be contaminated with an amount of less than 6 wt. % of $C_{12}$ alcohol, as well as to alkyl polyglucosides based on technical $C_{9/11}$ oxo alcohols (DP=1 to 3). The alkyl or alkenyl residue $R^1$ may further also derive from primary alcohols having from 12 to 22 carbon atoms, preferably from 12 to 14 carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as technical mixtures thereof, which may be obtained as described above. Alkyl polyglucosides based on hydrogenated $C_{12/14}$ coconut alcohol with a DP from 1 to 3 are preferred.

Alkyl polyglucosides that are suitable according to the present specification are sold under the INCI name Coco Glucoside and the trade name Plantacare 818 UP or under the INCI name Lauryl Glucoside and the trade name Plantacare 1200 UP.

A further example of the first subject matter of the present specification is therefore an agent which is characterized in that it includes as the non-ionic surfactant at least one alkyl polyglycoside, preferably selected from lauryl glucoside, decyl glucoside and/or coco glucoside.

The non-ionic surfactants are preferably present in the agent in an amount which correspondingly supports the solubility or emulsifiability of further ingredients and which adjusts the viscosity of the agents. At the same time, the content of non-ionic surfactants should be kept as low as possible to save on raw materials and to prevent the skin from drying out.

A further example of the first subject matter of the present specification is therefore an agent which is characterized in that it includes the non-ionic surfactant(s) according to types (i)-(iv) in an amount of from 0.001 to 15 wt. %, preferably from 0.05 to 12 wt. %, particularly preferably from 0.1 to 10.0 wt. %, in particular from 0.5 to 5.0 wt. %, and in particular preferably from 0.75 to 3.0 wt. %, relative in each case to the total weight of the agent.

Particularly preferred agents include non-ionic surfactant(s) according to type (i) in an amount of from 0.001 to 10 wt. %, preferably from 0.05 to 5 wt. %, particularly preferably from 0.1 to 3.0 wt. %, in particular from 0.5 to 2.0 wt. % and in particular preferably from 0.75 to 1.5 wt. %, relative in each case to the total weight of the agent, wherein the total amount of non-ionic surfactants according to types (i)-(iv) is preferably no greater than 15 wt. %, preferably no greater than 12 wt. % and more preferably no greater than 10 wt. %, relative in each case to the total weight of the agent.

Further preferred agents include non-ionic surfactant(s) according to type (ii) in an amount of from 0.001 to 10 wt. %, preferably from 0.05 to 5 wt. %, particularly preferably from 0.1 to 3.0 wt. %, in particular from 0.5 to 2.0 wt. % and in particular preferably from 0.75 to 1.5 wt. %, relative in each case to the total weight of the agent, wherein the total amount of non-ionic surfactants according to types (i)-(iv) is preferably no greater than 15 wt. %, preferably no greater than 12 wt. % and more preferably no greater than 10 wt. %, relative in each case to the total weight of the agent.

Further preferred agents include non-ionic surfactant(s) according to type (iii) in an amount of from 0.001 to 10 wt. %, preferably from 0.05 to 5 wt. %, particularly preferably from 0.1 to 3.0 wt. %, in particular from 0.5 to 2.0 wt. % and in particular preferably from 0.75 to 1.5 wt. %, relative in each case to the total weight of the agent, wherein the total amount of non-ionic surfactants according to types (i)-(iv) is preferably no greater than 15 wt. %, preferably no greater than 12 wt. % and more preferably no greater than 10 wt. %, relative in each case to the total weight of the agent.

Further preferred agents include non-ionic surfactant(s) according to type (iv) in an amount of from 0.001 to 10 wt. %, preferably from 0.05 to 5 wt. %, particularly preferably from 0.1 to 3.0 wt. %, in particular from 0.5 to 2.0 wt. % and in particular preferably from 0.75 to 1.5 wt. %, relative in each case to the total weight of the agent, wherein the total amount of non-ionic surfactants according to types (i)-(iv) is preferably no greater than 15 wt. %, preferably no greater than 12 wt. % and more preferably no greater than 10 wt. %, relative in each case to the total weight of the agent.

In a further preferred example, the agents according to the present specification additionally include, in addition to the compound of formula (I), at least one further substantive dye. Substantive dyes may be divided into anionic, cationic and non-ionic substantive dyes. The substantive dyes are preferably selected from nitrophenylenediamines, nitroaminophenols, azo dyes, anthraquinones, triarylmethane dyes or indophenols and physiologically acceptable salts thereof. The additional substantive dyes are each preferably used in an amount of from 0.001 to 2 wt. %, relative to the total application preparation.

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, as well as substantive dyes including a heterocyclic compound having at least one quaternary nitrogen atom, in particular Basic Yellow 87, Basic Orange 31 and Basic Red 51. The cationic substantive dyes which are sold under the ARIANOR® trademark are likewise preferred cationic substantive dyes according to the present specification.

Non-ionic nitro and quinone dyes and neutral azo dyes in particular are suitable as non-ionic substantive dyes. Preferred non-ionic substantive dyes are the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Coloring results with outstanding color intensity, brilliance and good wash fastness are obtained in particular if the agents according to the present specification include as the further substantive dye at least one dye selected from D&C Red No. 33 (Acid Red 33), Acid Black No. 1, D&C Orange No. 4 (Acid Orange No. 4), Acid Red 18, Basic Red 76, Acid Violet 43, HC Blue No. 12, N-(2-hydroxethyl)-4-methyl-2-nitroaniline (Methyl Yellow), HC Yellow No. 2, Red B 54 and 2-amino-6-chloro-4-phenol.

It is not necessary for the optionally included substantive dyes each to be uniform compounds. Instead it is possible for them also to include small amounts of further components arising from the manufacturing processes for the individual dyes, provided that they do not adversely influence the coloring result or need to be excluded for other, for example toxicological, reasons.

The agents according to the present specification may also be used as oxidation coloring agents. Such oxidation coloring agents additionally include at least one oxidation dye precursor, preferably at least one oxidation dye precursor of the developer type and at least one oxidation dye precursor of the coupler type. Particularly suitable oxidation dye precursors of the developer type are selected from at least one compound from the group formed from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-di hydro-1H,5H-pyrazolo[1,2-a]pyrazol-1-one and the physiologically acceptable salts thereof.

Particularly suitable oxidation dye precursors of the coupler type are selected from the group formed from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

The substantive dyes, developer components and coupler components are preferably each used in an amount of from 0.0001 to 5.0 wt. %, preferably from 0.001 to 2.5 wt. %, relative in each case to the ready-to-use agent. Developer components and coupler components may be used in approximately molar amounts to one another. Although the molar use has proved convenient, a certain excess of individual oxidation dye precursors is not disadvantageous, such that developer components and coupler components may be in a molar ratio of 1 to 0.5 to 1 to 3, in particular 1 to 1 to 1 to 2.

In the case of oxidation coloring agents, the agents preferably include an oxidizing agent, preferably hydrogen peroxide. The amount of hydrogen peroxide corresponds to the amounts in the lightening agents according to the present specification.

The agents may also be used as lightening coloring agents. In order to achieve the lightening effect the agents include hydrogen peroxide and/or one of the solid addition products thereof with organic or inorganic compounds.

A further example of the first subject matter of the present specification is therefore characterized in that the agent additionally includes hydrogen peroxide and/or one of the solid addition products thereof with organic or inorganic compounds.

In a preferred example, hydrogen peroxide itself is preferably used as an aqueous solution. The concentration of a hydrogen peroxide solution in the agent according to the present specification is determined on one hand by legal requirements and on the other by the desired effect; 6 to 12 wt. % solutions in water are preferably used. Ready-to-use agents of the first subject matter of the present specification that are preferred according to the present specification are characterized in that they include from 0.5 to 20 wt. %, preferably from 1 to 12.5 wt. %, particularly preferably from 2.5 to 10 wt. % and in particular from 3 to 6 wt. % of hydrogen peroxide, relative in each case to the total weight of the ready-to-use agent.

In order to achieve a stronger lightening and bleaching effect, the agent may also include at least one peroxo salt. Suitable peroxo salts are inorganic peroxo compounds, preferably selected from the group formed from ammonium peroxodisulfate, alkali metal peroxodisulfates, ammonium peroxomonosulfate, alkali metal peroxomonosulfates, alkali metal peroxodiphosphates and alkaline-earth metal peroxides. Peroxodisulfates are particularly preferred, in particular ammonium peroxodisulfate, potassium peroxodisulfate and sodium peroxodisulfate.

The persulfates are each included in the agent according to the present specification in an amount of from 0.5 to 20 wt. %, preferably from 1 to 12.5 wt. %, particularly preferably from 2.5 to 10 wt. % and in particular from 3 to 6 wt. %, relative in each case to the total weight of the ready-to-use agent.

A further preferred example is an agent for coloring and optionally lightening keratinic fibers, which additionally includes hydrogen peroxide, one of the solid addition products thereof with organic or inorganic compounds, ammonium peroxodisulfate, potassium peroxodisulfate and/or sodium peroxodisulfate, each in an amount of from 0.5 to 20 wt. %, preferably from 1 to 12.5 wt. %, particularly preferably from 2.5 to 10 wt. % and in particular from 3 to 6 wt. %, relative in each case to the total weight of the ready-to-use agent.

To strengthen the bleaching effect, the agent may include further bleaching strength intensifiers, such as for example tetraacetyl ethylene diamine (TAED), 1,5-diacetyl-2,4-dioxohexahydro-1,3,5-triazine (DADHT), tetraacetyl glycoluril (TAGU), N-nonanoyl succinimide (NOSI), n-nonanoyl or isononanoyl oxybenzene sulfonate (n- or i-NOBS), phthalic acid anhydride, triacetin, ethylene glycol diacetate and 2,5-diacetoxy-2,5-dihydrofuran as well as carbonate salts or hydrogen carbonate salts, in particular ammonium hydrogen carbonate, ammonium carbonate, sodium hydrogen carbonate, disodium carbonate, potassium hydrogen carbonate, dipotassium carbonate and calcium carbonate, and nitrogen-containing, heterocyclic bleaching strength intensifiers, such as 4-acetyl-1-methylpyridinium-p-toluenesulfonate, 2-acetyl-1-methylpyridinium-p-toluenesulfonate as well as N-methyl-3,4-dihydroisoquinolinium-p-toluenesulfonate.

To further increase the lightening, at least one $SiO_2$ compound such as silicic acid or silicates, in particular water glasses, may additionally be added to the composition according to the present specification. It may be preferable according to the present specification to use the $SiO_2$ compounds in amounts of from 0.05 wt. % to 15 wt. %, particularly preferably in amounts of from 0.15 wt. % to 10 wt. % and most particularly preferably in amounts of from 0.2 wt. % to 5 wt. %, relative in each case to the composition according to the present specification. The specified amounts indicate the content of $SiO_2$ compounds (excluding their water component) in the agents.

The ready-to-use coloring agents may also include additional active agents, auxiliary substances and additives to improve the coloring capacity and to establish further desired properties of the agents.

The ready-to-use coloring agents are preferably provided as a liquid preparation, and therefore a further surface-active substance is additionally added to the agents, such surface-active substances being referred to as surfactants or emulsifiers, depending on the field of application. They are preferably selected from anionic, cationic, zwitterionic and amphoteric surfactants and emulsifiers.

Agents that are preferred according to the present specification are characterized in that the agent additionally includes at least one anionic surfactant. Preferred anionic surfactants are fatty acids, alkyl sulfates, alkyl ether sulfates and ether carboxylic acids with 10 to 20 carbon atoms in the alkyl group and up to 16 glycol ether groups in the molecule. The anionic surfactants are used in amounts of from 0.1 to 45 wt. %, preferably from 1 to 30 wt. % and most particularly preferably from 1 to 15 wt. %, relative to the total amount of the ready-to-use agent.

Agents that are preferred according to the present specification are characterized in that the agent additionally includes at least one zwitterionic surfactant. Preferred zwitterionic surfactants are betaines, N-alkyl-N,N-dimethylammonium glycinates, N-acyl aminopropyl-N,N-dimethylammonium glycinates, and 2-alkyl-3-carboxymethyl-3-hydroxyethyl imidazolines. A preferred zwitterionic surfactant is known under the INCI name Cocamidopropyl Betaine.

Agents that are preferred according to the present specification are characterized in that the agent additionally includes at least one amphoteric surfactant. Preferred amphoteric surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids. Particularly preferred amphoteric surfactants are N-cocoalkyl aminopropionate, cocoacylaminoethyl aminopropionate and $C_{12}$-$C_{18}$ acyl sarcosine.

The zwitterionic or amphoteric surfactants are used in amounts of from 0.1 to 45 wt. %, preferably from 1 to 30 wt. % and most particularly preferably from 1 to 15 wt. %, relative to the total amount of the ready-to-use agent.

Agents that are suitable according to the present specification may also include cationic surfactants of the quaternary ammonium, esterquat and amidoamine types. Preferred quaternary ammonium compounds are ammonium halides and the imidazolium compounds known under the INCI names Quaternium-27 and Quaternium-83. Further cationic surfactants which may be used according to the present specification are quaternized protein hydrolysates. A compound from the amidoamines that is particularly suitable according to the present specification is the stearamidopropyl dimethylamine which is commercially available under the name Tegoamid® S 18. Preferred esterquats are quaternized ester salts of fatty acids with triethanolamine, quaternized ester salts of fatty acids with diethanol alkyl amines and quaternized ester salts of fatty acids with 1,2-dihydroxypropyl dialkylamines. The cationic surfactants are preferably included in the agents used according to the present specification in amounts of from 0.05 to 10 wt. %, relative to the total agent.

The ready-to-use agents may include further auxiliary substances and additives. Thus it has proved advantageous if the agents include at least one thickening agent. There are no restrictions in principle regarding these thickening agents. Both organic and also purely inorganic thickening agents may be used.

Suitable thickening agents are
cationic, synthetic polymers;
anionic, synthetic polymers, such as polyacrylates, acrylates copolymer, copolymers of acrylic acid and methacrylic acid;
naturally occurring thickening agents, such as non-ionic guar gums, scleroglucan gums or gum arabic, ghatti gum, karaya gum, tragacanth gum, carrageen gum, carob seed meal, pectins, xanthan gums, alginates, starch fractions and derivatives such as amylose, amylopectin and dextrins, as well as cellulose derivatives, such as for example carboxymethyl cellulose, methyl cellulose and hydroxyalkyl celluloses;
non-ionic, fully synthetic polymers, such as polyvinyl alcohol or polyvinylpyrrolidone; as well as
inorganic thickening agents, in particular phyllosilicates such as for example bentonite, particularly smectites, such as montmorillonite or hectorite.

Coloring processes on keratin fibers conventionally take place in the weakly acid to alkaline range, preferably in a weakly acid to weakly alkaline environment. In order to protect the keratin fibers and also the skin as far as possible, it is not desirable to establish too high a pH, however. The pH of the agents according to the present specification may therefore be between 3 and 11, preferably between 5 and 8. The pH values in the context of the present specification are pH values measured at a temperature of 22 degrees Celsius (° C.).

The alkalizing agents which may be used according to the present specification to establish the preferred pH are preferably selected from ammonia, alkanolamines, basic amino acids as well as inorganic alkalizing agents. Preferred inorganic alkalizing agents are magnesium carbonate, sodium hydroxide, potassium hydroxide, sodium silicate and sodium metasilicate. Organic alkalizing agents which may be used according to the present specification are preferably selected from monoethanolamine, 2-amino-2-methylpropanol and triethanolamine. The basic amino acids which may be used as the alkalizing agent according to the present specification are preferably selected from the group formed from arginine, lysine, ornithine and histidine, particularly preferably arginine. Acidifying agents which may be used to establish the pH are organic acids, such as citric acid, acetic acid, ascorbic acid, benzoic acid, lactic acid, malic acid and maleic acid, as well as mineral acids such as hydrochloric acid, sulfuric acid or phosphoric acid.

It has furthermore proved advantageous for the coloring agents, in particular if they additionally include hydrogen peroxide, to include at least one stabilizer or complexing agent. Particularly preferred stabilizers are phenacetin, alkali benzoates (sodium benzoate) and salicylic acid. All prior art complexing agents may also be used. Preferred complexing agents according to the present specification are nitrogen-containing polycarboxylic acids, in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP) or the sodium salts thereof.

The agents according to the present specification may also include further active agents, auxiliary substances and additives, such as for example non-ionic polymers, such as for example vinylpyrrolidone/vinyl acrylate copolymers, polyvinylpyrrolidone, vinylpyrrolidone/vinyl acetate copolymers, polyethylene glycols and polysiloxanes; additional silicones, such as volatile or non-volatile, straight-chain, branched or cyclic, crosslinked or uncrosslinked polyalkyl siloxanes (such as dimethicones or cyclomethicones), polyaryl siloxanes and/or polyalkylaryl siloxanes, in particular polysiloxanes having organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallyl ammonium chloride polymers, acrylamide-dimethyldiallyl ammonium chloride copolymers, dimethylaminoethyl methacrylate-vinylpyrrolidone copolymers quaternized with diethyl sulfate, vinylpyrrolidone-imidazolinium-methochloride copolymers and quaternized polyvinyl alcohol, in particular Polyquaternium-2, Polyquaternium-4, Polyquaternium-6, Polyquaternium-7, Polyquaternium-10, Polyquaternium-11, Polyquaternium-16, Polyquaternium-24, Polyquaternium-28, Polyquaternium-37, Polyquaternium-44, Polyquaternium-46, Polyquaternium-55, Polyquaternium-67, Polyquaternium-68, Polyquaternium-69 and Polyquaternium-87; zwitterionic and amphoteric polymers, such as in particular Polyquaternium-22 and Polyquaternium-39; structuring agents such as glucose, maleic acid and lactic acid, hair-conditioning compounds such as phospholipids, for example lecithin and cephalins; perfume oils, dimethyl isosorbide and cyclodextrins; active agents to improve the fiber structure, in particular mono-, di- and oligosaccharides such as for example glucose, galactose, fructose, fruit sugars and lactose; dyes for coloring the agent; anti-dandruff active agents such as piroctone olamine, zinc omadine and climbazole; amino acids and oligopeptides; protein hydrolysates of animal and/or plant origin as well as those in the form of their fatty acid condensation products or optionally anionically or cationically modified derivatives thereof; vegetable oils; light stabilizers and UV blockers; active agents such as panthenol, pantothenic acid, pantolactone, allantoin, pyrrolidone carboxylic acids and salts thereof as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; pigments as well as propellants such as propane-butane mixtures, $N_2O$, dimethyl ether, $CO_2$ and air.

Further substances may be selected in accordance with the desired properties of the agents. With regard to further optional components and to the amounts of these components used, reference is expressly made to the relevant manuals, for example Kh. Schrader, Grundlagen and Rezepturen der Kosmetika [Fundamentals and formulations of cosmetics], $2^{nd}$ Edition, Hüthig Buch Verlag, Heidelberg, 1989. The additional active agents and auxiliary substances are used in the agents according to the present specification preferably in amounts of from 0.0001 to 25 wt. % in each case, in particular from 0.0005 to 15 wt. %, relative to the total weight of the application mixture.

A method for coloring and optionally lightening keratinic fibers, in particular human hair, which is characterized in that an agent of the first subject matter of the present specification is applied to the keratin-containing fibers, left on the fibers for 5 to 60 minutes and then rinsed out again with water or washed out with a shampoo, is suitable in particular for the application of the agents according to the present specification. The contact time of the ready-to-use coloring agents is preferably 5 to 45 minutes, in particular 10 to 40 minutes, particularly preferably 15 to 35 minutes. During the contact time of the agent on the fibers, it may be advantageous to support the lightening process by supplying heat. Heat may be supplied both from an external heat source, such as for example hot air from a hot air blower, and also, in particular if the hair lightening process is taking place on a living test subject, from the body temperature of the test subject. In the latter case, the section to be lightened is conventionally covered with a hood. A contact phase at room temperature is likewise in accordance with the present specification. In particular, the temperature during the contact time is between 20° C. and 40° C., in particular between 25° C. and 38° C. After the end of the contact time, the remaining coloring preparation is rinsed out of the hair with water or a cleaning agent. Commercial shampoo may be used in particular as the cleaning agent, wherein in particular if the coloring agent has a carrier having a high surfactant content, the cleaning agent may be dispensed with and the rinsing process may take place with water.

The agents according to the present specification may be formulated as one-component agents (coloring and lightening agent) or as multi-component agents such as two-component agents or three-component agents, and used accordingly. A separation into multi-component systems is useful in particular where incompatibilities between the ingredients are to be expected or of concern; in such systems the agent to be used is prepared by the consumer immediately before use by mixing the components together.

If the agent according to the present specification includes both substantive dyes—as well as optionally additionally oxidation dye precursors—and oxidizing agents, they are conveniently packaged separately from one another in order to avoid a premature, undesired reaction and brought into contact only immediately before application.

A coloring method in which the coloring cream and the oxidizing agent are initially kept separate is therefore preferred. The present specification therefore also provides a method for coloring and lightening human hair, wherein a composition on an aqueous basis including hydrogen peroxide is mixed with an agent according to the present specification including at least one compound of formula (I) to form a homogeneous composition, and this is applied to the hair. The non-ionic surfactant (b) may in this case be packaged with the hydrogen peroxide solution, with the compound of formula (I), or with both.

In a further example of the present specification, agents are therefore preferred which are characterized in that they are produced immediately before application by mixing at least two preparations, wherein the at least two preparations are provided in at least two separately packaged containers, and wherein one container contains an agent (A), which includes in a cosmetic carrier at least one cationic anthraquinone dye of formula (I) and at least one non-ionic surfactant (b)—as well as optionally additionally oxidation dye precursors, and a further container contains an oxidizing agent preparation (B) including at least one oxidizing agent.

The formulation of a combination of (a) compounds of general formula (I) with (b) the specific non-ionic surfactants is outstandingly suitable for producing intense colors with high brilliance, high shine and a low selectivity in conjunction with an outstanding wash fastness.

The present specification also provides for the use of an agent of the first subject matter of the present specification to produce hair dyes having increased shine, an intense color result with improved fastness properties and/or reduced selectivity.

All that has been stated with respect to the agents according to the present specification applies with necessary alterations to further preferred examples of the methods and use according to the present specification.

EXAMPLES

The examples that follow indicate agents that were produced according to the present specification for the treatment of keratinic fibers. Unless otherwise indicated, the stated quantities are percentages by weight.

|  | wt. % |
|---|---|
| Formulation example 1 | |
| Propylene carbonate | 10.0 |
| Ethanol, 96% | 43.0 |
| D&C Red No. 33 | 0.05 |
| Acid Black No. 1 | 0.005 |
| D&C Orange No. 4 | 0.20 |
| Acid Violet 43 | 0.030 |
| Acid Red 18 | 0.20 |
| Crodafos HCE-LQ | 1.00 |
| SME 253 | 3.50 |
| Malic acid | 0.40 |
| Cationic Blue 347 | 0.20 |
| Perfume | qs |
| Water | to 100 |
| Formulation example 2 | |
| Coconut alcohol | 4.00 |
| Cocamidopropyl betaine, 40% | 4.00 |
| Sodium myreth sulfate (2 EO), 27% | 4.00 |
| Laureth-2 | 0.80 |
| Emulgade 1000 NI | 3.00 |
| Methylparaben | 0.15 |
| Propylparaben | 0.19 |
| Polyethylene glycol MG 400 | 3.00 |
| Acid Red 33 | 0.005 |
| N-(2-Hydroxyethyl)-4-methyl-2-nitroaniline (Methyl Yellow) | 0.04 |
| Carbomer [1000-7000 mPas (0.2%)] | 0.50 |
| Monoethanolamine | 0.23 |
| 1,3-Butanediol | 1.00 |
| Polyquaternium-6 | 0.50 |
| Cationic Blue 347 | 0.20 |
| Perfume | qs |
| Water | to 100 |
| Formulation example 3 | |
| Polyquaternium-10 | 0.45 |
| Citric acid monohydrate | 0.70 |
| Timiron Super Silver | 0.20 |
| Cationic Blue 347 | 0.20 |
| Salicylic acid | 0.20 |
| Disodium cocoamphodiacetate | 7.00 |
| Sodium benzoate | 0.50 |
| Nicotinamide | 0.50 |
| Sodium pyrrolidone-2-carboxylate | 2.00 |
| Cutina HR | 1.00 |
| PEG-7 glyceryl cocoate | 0.50 |
| Sodium myreth sulfate (2 EO), 70% | 24.0 |
| NaOH, 50% | 0.147 |
| D-Panthenol, 75% | 0.50 |
| Euperlan PK 3000 AM | 2.60 |
| ProSina | 2.0 |
| Sericin H | 0.20 |
| Caramel syrup, 75% | 0.60 |

-continued

| | |
|---|---|
| Apricot kernel oil | 0.10 |
| PEG-40 hydrogenated castor oil | 0.60 |
| Sodium chloride | 0.20 |
| Antil 141 L | 1.0 |
| Hydrolyzed silk protein | 1.50 |
| Benzophenone-4 | 0.50 |
| Perfume | qs |
| Water | to 100 |

| Formulation example 4 | 4a (wt. %) | 4b (wt. %) |
|---|---|---|
| Cetearyl alcohol | 6.00 | 6.00 |
| Coconut alcohol | 6.00 | 6.00 |
| Ceteareth-12 | 2.00 | 2.00 |
| Ceteareth-20 | 3.00 | 3.00 |
| PEG-40 hydrogenated castor oil | 2.00 | 2.00 |
| Macadamia nut oil | 1.00 | 1.00 |
| Methylparaben | 0.15 | 0.15 |
| Propylparaben | 0.15 | 0.15 |
| Tocopherol | 0.20 | 0.20 |
| Phenoxyethanol | 1.00 | 1.00 |
| Hydroxyethylcellulose | 1.00 | 1.00 |
| NaOH, 50% | 0.10 | 0.10 |
| Polyethylene glycol MG 400 | 5.00 | 5.00 |
| D-Panthenol, 75% | 0.30 | 0.30 |
| Citric acid monohydrate | 0.10 | 0.10 |
| HC Blue No. 2 | 1.50 | — |
| HC Blue No. 12 | — | 1.20 |
| Basic Blue 99 | 0.42 | — |
| Bluequat Bromide | — | 0.21 |
| Basic Brown 16 | 0.075 | — |
| Basic Brown 17 | — | 0.075 |
| Ext. D&C Violet 2 | 0.075 | 0.075 |
| Basic Red 76 | 0.075 | 0.075 |
| Basic Yellow 57 | 0.075 | 0.075 |
| HC Yellow No. 2 | 0.20 | 0.20 |
| N,N-Bis(2-hydroxyethyl)-2-nitro-p-phenylenediamine | 0.10 | 0.20 |
| Cationic Blue 347 | 0.50 | 0.50 |
| Perfume | qs | qs |
| Water | to 100 | to 100 |

| | wt. % |
|---|---|
| Formulation example 5 | |
| Phospholipid EFA | 0.50 |
| Methylparaben | 0.15 |
| Propylparaben | 0.15 |
| Dehyquart A CA | 5.00 |
| Cetyl alcohol | 4.00 |
| HC Blue No. 12 | 0.50 |
| Bluequat Bromide | 0.20 |
| N-(2-Hydroxyethyl)-4-methyl-2-nitroaniline (Methyl Yellow) | 0.05 |
| HC Yellow No. 2 | 0.08 |
| Red B 54 | 0.06 |
| 2-Amino-6-chloro-4-phenol | 0.08 |
| HC Yellow No. 13 | 0.07 |
| Cationic Blue 347 | 0.50 |
| Procetyl AWS-LQ | 1.00 |
| Monoethanolamine | 0.25 |
| Perfume | qs |
| Water | to 100 |
| Formulation example 6 | |
| Methylparaben | 0.10 |
| Carbomer [20000-30000 mPas (0.2%)] | 0.20 |
| KOH, 50% | 0.10 |
| Jaguar C-17 | 0.70 |
| Genamin KDMP | 3.00 |
| Cetearyl alcohol + PEG-20 stearate | 2.50 |
| Cetearyl alcohol | 3.00 |
| Liquid paraffin | 2.00 |
| Emulgade 1000 NI | 2.40 |
| Genamin CTAC | 3.00 |
| Acid Violet 43 | 0.008 |
| Cationic Blue 347 | 0.20 |
| Prestige Bright Mystic Violet | 0.12 |

-continued

| | |
|---|---|
| Prestige Amethyst | 0.11 |
| Prestige Fire-Red | 0.012 |
| $KH_2PO_4$ | 0.30 |
| Benzophenone-4 | 0.10 |
| D-Panthenol, 75% | 1.00 |
| Dimethicone/Dimethiconol | 2.00 |
| Phenoxyethanol | 0.40 |
| Crodarom Rock Crystal | 1.00 |
| Methylisothiazolone, approx. 10% in $H_2O$ | 0.10 |
| Perfume | qs |
| Water | to 100 |

Raw Materials Used

Cationic Blue 3-[(4-amino-9,10-dihydro-3-methyl-9,10-dioxo-1-anthracenyl)amino]-N,N,N-trimethyl-1-propanaminium methosulfate Dehyquart A CA approx. 25% active content; INCI name: Aqua, Cetrimonium Chloride (BASF)

Phospholipid EFA INCI name: Linoleamidopropyl PG-Dimonium Chloride Phosphate E (30%), Propylene Glycol (25%) (Uniqema)

Procetyl AWS-LQ INCI name: PPG-5 Ceteth-20 (Croda)

Crodafos HCE-LQ INCI name: Oleth-5 Phosphate, Dioleyl Phosphate (Croda)

SME 253 approx. 26-33% active substance; INCI name: Amodimethicone, C11-15 Pareth-7, Laureth-9, Glycerin, Trideceth-12 (Bayer Silicones)

Emulgade 1000 NI INCI name: Cetearyl alcohol, Cetearath-20 (BASF)

Timiron Super Silver INCI name: Mica, Titanium Dioxide (Merck KGaA)

Cutina HR INCI name: Hydrogenated Castor Oil (BASF)

Euperlan PK 3000 AM approx. 43% solid substance; INCI name: Aqua, Glycol Distearate, Glycerin, Laureth-4, Cocamidopropyl Betaine, Formic Acid (BASF)

ProSina INCI name: Aqua, hydrolyzed Keratin (Keratec/Croda)

Sericin H INCI name: Sericin (Pentapharm)

Antil 141 L approx. 40% active substance; INCI name: Propylene Glycol, PEG-55 Propylene Glycol Oleate (Goldschmidt/Evonik)

Jaguar C-17 INCI name: Guar Hydroxypropyltrimonium Chloride (Rhodia)

Genamin KDMP approx. 80% active content; INCI name: Behentrimonium Chloride, Isopropanol (Clariant)

Genamin CTAC approx. 29% active content; INCI name: Aqua, Cetrimonium Chloride (Clariant)

Emulgade 1000 NI INCI name: Cetearyl alcohol, Cetearath-20 (BASF)

Prestige Bright Mystic Violet INCI name: Mica, CI 77491 (Iron Oxides), Tin Oxide (Eckart Cosmetic Colours)

Prestige Amethyst INCI name: Mica, CI 77891 (Titanium Dioxide), Tin Oxide, CI 77510 (Ferric Ferrocyanide), CI 75470 (Carmine) (Eckart Cosmetic Colours)

Prestige Fire-Red INCI name: Mica, CI 77491 (Iron Oxides) (Eckart Cosmetic Colours)

Crodarom Rock Crystal INCI name: Aqua, Propylene Glycol, Quartz (Crodarom)

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability or configuration of the invention in any way. Rather, the foregoing detailed description will provide those skilled in the art with a convenient road map for implementing an exemplary embodiment of the invention, it being understood that various changes may be made in the function and arrangement of the elements described in an exemplary embodiment without departing from the scope of the invention as set forth in the appended claims and their legal equivalents.

The invention claimed is:
1. An agent for coloring keratinic fibers comprising, in a cosmetic carrier,
(a) at least one compound of formula (I):

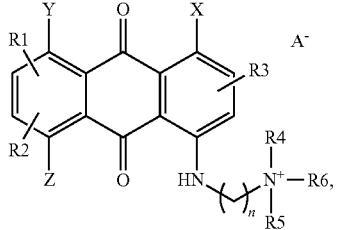

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
in which
at least one of the R1, R2 and R3 denotes a halogen, a carboxyl group, a sulfonic acid group, a $C_1$-$C_6$ alkyl group or a $C_1$-$C_6$ alkoxy group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen or an N(R7)(R8) group,
in which:
R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
wherein at least one of the residues X, Y and Z denotes an N(R7)(R8) group;
n denotes an integer between 2 and 6 inclusive; and
$A^-$ denotes a physiologically acceptable anion;
and
(b) at least one non-ionic surfactant comprising a surfactant selected from the group consisting of:
(i) a polyethoxylated fatty alcohol having a degree of ethoxylation from 2 to 29;
(ii) an addition product of ethylene oxide and propylene oxide with one or more fatty alcohol;
(iii) a fatty acid glycol monoester, a fatty acid glyceryl monoester, or a sorbitan fatty acid ester, each of which is optionally polyethoxylated;
(iv) an alkyl polyglycoside; and
(v) combinations thereof;
wherein the agent does not contain oxidative dye precursors.

2. The agent of claim 1, wherein the at least one non-ionic surfactant (b) comprises at least one polyethoxylated fatty alcohol of type (i), further wherein the degree of ethoxylation is from 2 to 25.

3. The agent of claim 1, wherein the at least one non-ionic surfactant comprises an alkyl polyglycoside selected from the group consisting lauryl glucoside, decyl glucoside, coco glucoside, and combinations thereof.

4. The agent of claim 1, wherein the agent simultaneously lightens the keratinic fibers.

5. The agent of claim 1, wherein at least one of the residues R1, R2 and R3 denotes a $C_1$-$C_6$ alkyl group.

6. The agent of claim 1, wherein X of formula (I) denotes an $NH_2$ group.

7. The agent of claim 1, wherein the compound of formula (I) is provided by a compound according to formula (Ia),

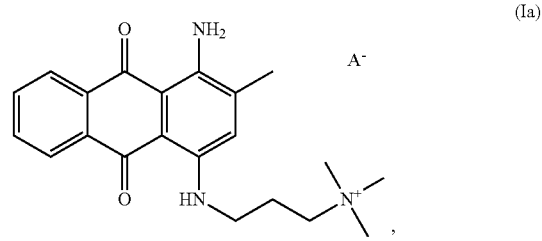

in which $A^-$ denotes a physiologically acceptable anion.

8. The agent of claim 1, wherein the compound(s) according to formula (I) (a) comprise an amount of from 0.0001 to 5 weight percent (wt. %), relative to the total weight of the agent.

9. The agent of claim 1, wherein the non-ionic surfactant(s) (b) comprise an amount of from 0.001 to 15 wt. %, relative to the total weight of the agent.

10. The agent of claim 1, wherein the at least one non-ionic surfactant comprises a polyethoxylated fatty alcohol(s) having an average degree of ethoxylation from 2 to 29 selected from the group consisting of Laureth-2, Oleth-2, Ceteareth-2, Laneth-2, Laureth-3, Oleth-3, Ceteareth-3, Laureth-4, Oleth-4, Ceteareth-4, Laneth-4, Laureth-5, Oleth-5, Ceteareth-5, Laneth-5, Deceth-7, Laureth-7, Oleth-7, Coceth-7, Ceteth-7, Ceteareth-7, C11-15 Pareth-7, Laureth-9, Oleth-9, Ceteareth-9, Laureth-10, Oleth-10, Beheneth-10, Ceteareth-10, Laureth-12, Ceteareth-12, Trideceth-12, Ceteth-15, Laneth-15, Ceteareth-15, Laneth-16, Ceteth-16, Oleth-16, Steareth-16, Oleth-20, Ceteth-20, Ceteareth-20, Laneth-20, Steareth-21, Ceteareth-23, Ceteareth-25 and Ceteareth-27.

11. The agent of claim 1, wherein the at least one non-ionic surfactant comprises an addition product of ethylene oxide and propylene oxide to a fatty alcohol, the addition product being selected from the group consisting of PPG-6 Deceth-9, PPG-1 Trideceth-6, PPG-6 Deceth-4, PPG-1-Laureth-9; PPG-12-Laneth-50, PPG-12-Laneth-65, PPG-6 C12-18 PARETH-11, PPG-4 Laureth-2, PPG-4 Laureth-5, PPG-8 Deceth-6, PPG-6 $C_{12-18}$ Pareth-11, PPG-1-Laureth-9, PPG-5-Ceteth-20, PPG-5-Laureth-5 as well as PPG-26-Buteth-26, PPG-20 Buteth-30, PPG-5 Buteth-7, PPG-12 Buteth-3, PPG-2 Buteth-3, PPG-3 Buteth-5, PPG-28 Buteth-35, PPG-33 Buteth-45, PPG-7 Buteth-10 and PPG-24-Buteth-27.

12. The agent of claim 1, wherein the at least one non-ionic surfactant (b) comprises a surfactant selected from the group consisting of Glyceryl Stearate, PEG-30 Glyceryl Stearate, PEG-20 Glyceryl Stearate, Glyceryl Oleate, Glyceryl Cocoate, Glyceryl Palmitate, PEG-18 Glyceryl Oleate, PEG-18 Glyceryl Cocoate, PEG-7 Glyceryl Cocoate, PEG-30 Glyceryl Cocoate and PEG-80 Glyceryl Cocoate.

13. The agent of claim 1, wherein the at least one non-ionic surfactant (b) comprises a surfactant selected from the group consisting of Polysorbate-20 (sorbitan monolaurate+20 EO), Polysorbate-60 (sorbitan monostearate+20 EO), Polysorbate-65 (sorbitan tristearate+20 EO), Polysorbate-80 (sorbitan monooleate+20 EO) and Polysorbate-85 (sorbitan trioleate+20 EO).

14. A method for coloring human hair, comprising:
A. applying an agent for coloring keratinic fibers comprising, in a cosmetic carrier,
  a. at least one compound of formula (I):

$$\text{(I)}$$

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
  in which
  at least one of the R1, R2 and R3 denotes a halogen, a carboxyl group, a sulfonic acid group, a $C_1$-$C_6$ alkyl group or a $C_1$-$C_6$ alkoxy group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
  or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen or an N(R7)(R8) group,
  in which:
  R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
  wherein at least one of the residues X, Y and Z denotes an N(R7)(R8) group;

n denotes an integer between 2 and 6 inclusive; and
$A^-$ denotes a physiologically acceptable anion;
and
b. at least one non-ionic surfactant comprising a surfactant selected from the group consisting of:
  (i) a polyethoxylated fatty alcohol having a degree of ethoxylation from 2 to 29;
  (ii) an addition product of ethylene oxide and propylene oxide with one or more fatty alcohol;
  (iii) a fatty acid glycol monoester, a fatty acid glyceryl monoester, or a sorbitan fatty acid ester, each of which is optionally polyethoxylated;
  (iv) an alkyl polyglycoside; and
  (v) combinations thereof;
wherein the agent does not contain oxidative dye precursors;
B. allowing the agent to act on the hair for a period from 5 to 60 minutes; and
C. rinsing the agent from the hair.

15. The method of claim 14, wherein the agent is allowed to act on the hair for a period from 5 to 45 minutes.

16. The method of claim 14, wherein the agent provides a hair dye that gives increased shine, intense colors with improved fastness properties or reduced selectivity.

17. An agent for coloring keratinic fibers comprising, in a cosmetic carrier,
(a) at least one compound of formula (I):

$$\text{(I)}$$

in which:
R1, R2, R3 each independently of one another, denote hydrogen, halogen, a nitro group, a cyano group, a carboxyl group, a sulfonic acid group, a hydroxyl group, a $C_1$-$C_6$ acyl amino group, a carboxamide group, a sulfonamide group, a $C_1$-$C_6$ alkyl group, $C_1$-$C_6$ alkoxy group, a $C_2$-$C_6$ alkenyl group, a $C_2$-$C_6$ hydroxyalkyl group or a $C_1$-$C_6$ alkoxy $C_2$-$C_6$ alkyl group;
  in which
  at least one of the R1, R2 and R3 denotes a halogen, a carboxyl group, a sulfonic acid group, a $C_1$-$C_6$ alkyl group or a $C_1$-$C_6$ alkoxy group;
R4, R5, R6 each independently of one another, denote a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;
  or R4 and R5, together with the quaternary nitrogen atom to which they are bound, form a 5-, 6- or 7-membered ring, which optionally includes further heteroatoms and optionally also bears further substituents;
X, Y, Z each independently of one another, denote hydrogen or an N(R7)(R8) group,
in which:
  R7 and R8, each independently of one another, denote hydrogen, a $C_1$-$C_6$ alkyl group, a $C_2$-$C_6$ alkenyl group, a $C_2$-$C_6$ hydroxyalkyl group or a $C_1$-$C_6$ alkoxy $C_2$-$C_6$ alkyl group;

wherein at least one of the residues X, Y and Z denotes an N(R7)(R8) group;

and R7 and R8 are chosen so that at least one of the X, Y and Z denotes an $NH_2$ group;

n denotes an integer between 2 and 6 inclusive; and $A^-$ denotes a physiologically acceptable anion;

and (b) at least one non-ionic surfactant comprising a surfactant selected from the group consisting of:
  (i) a polyethoxylated fatty alcohol having a degree of ethoxylation from 2 to 29;
  (ii) an addition product of ethylene oxide and propylene oxide with one or more fatty alcohol;
  (iii) a fatty acid glycol monoester, a fatty acid glyceryl monoester, or a sorbitan fatty acid ester, each of which is optionally polyethoxylated;
  (iv) an alkyl polyglycoside; and
  (v) combinations thereof;

wherein the at least one nonionic surfactant comprises a surfactant selected from the group consisting of oleth-2, oleth-5, steareth-21, and combinations thereof.

18. The agent of claim 17, wherein the compound(s) according to formula (I) (a) comprise an amount of form 0.0001 to 5 wt. %, relative to the total weight of the agent.

* * * * *